United States Patent [19]

Schoetensack et al.

[11] 4,205,088
[45] May 27, 1980

[54] COMPOSITIONS OF AND NEW USES FOR N-ACYLANILINOBUTYRIC ACIDS

[75] Inventors: Wolfgang Schoetensack, Hegne; Richard Riedel, Constance, both of Fed. Rep. of Germany

[73] Assignee: Byk Gulden Lomberg Chemische Fabrik GmbH, Constance, Fed. Rep. of Germany

[21] Appl. No.: 785,959

[22] Filed: Apr. 8, 1977

Related U.S. Application Data

[62] Division of Ser. No. 571,501, Apr. 25, 1975, Pat. No. 4,034,111.

[30] Foreign Application Priority Data

Apr. 30, 1974 [LU] Luxembourg ............................ 69970
Oct. 25, 1974 [DE] Fed. Rep. of Germany ....... 2450680

[51] Int. Cl.$^2$ ............................................ A61K 31/195
[52] U.S. Cl. .................................................... 424/319
[58] Field of Search ......................................... 424/319

[56] References Cited
U.S. PATENT DOCUMENTS 3,780,095  12/1973  Klemm ................................. 424/319

OTHER PUBLICATIONS

PDR (1968) pp. 648, 771, 828, 948, 1138 & 1149.

Primary Examiner—Frederick E. Waddell
Attorney, Agent, or Firm—Berman, Aisenberg & Platt

[57] ABSTRACT

Pharmaceutically-acceptable compositions containing, as an active ingredient, at least one N-acylanilinobutyric acid have uses unrelated to the choleretic activity suggested in U.S. Pat. No. 3,780,095. Moreover, the further uses generally involve administration of smaller doses than would be required to obtain a choleretic effect.

The new uses include: (a) increasing the gastrointestinal enzyme secretion and (b) tonicizing the cardiovascular system. The increase of the gastrointestinal enzyme secretion is applied in the treatment of different diseases, such as treatment of sprue, treatment of indigestion, treatment of acute and chronic pancreatitis, therapy for degenerated intestine mucous membrane, treatment of stomach spasms, treatment of stomach ulcers, treatment of diseases where the application of an antigastrin is indicated. The tonicising of the cardiovascular system is applied in, e.g., increasing the circulation of blood in internal organs, increasing the heart force, treating disturbances in the liver function.

19 Claims, No Drawings

COMPOSITIONS OF AND NEW USES FOR N-ACYLANILINOBUTYRIC ACIDS

CROSS-REFERENCE TO RELATED APPLICATION

This is a division of application Ser. No. 571,501, filed Apr. 25th, 1975, now U.S. Pat. No. 4,034,111.

BACKGROUND OF THE INVENTION

The active ingredient for novel medicaments and uses is a compound of the type disclosed in U.S. Pat. No. 3,780,095, which clearly explains the manner in which such compounds are made.

SUMMARY

Novel medicaments containing, as at least one active ingredient, a pharmaceutically-acceptable N-acylanilinobutyric acid or a pharmaceutically-acceptable salt thereof have a number of uses which are unrelated to and unexpected from the choleretic activity referred to in U.S. Pat. No. 3,780,095. These medicaments contain one such active ingredient, a combination of any two or more such active ingredients or a combination of one or more such active ingredients and one or more other therapeutically-active and physiologically-compatible ingredients in a chemically-compatible dosage form.

The uses include, but are not limited to, those enumerated in the preceding Abstract of the Disclosure.

An object of this invention is to find relatively non-toxic pharmaceutically-acceptable and physiologically-active compounds and corresponding medicaments useful for the treatment of different diseases connected with a disfunction of the gastrointestinal enzyme system and/or cardiovascular system, respectively, e.g., for increasing exocrine enzyme (amylase, trypsin, lipase, etc.) secretion by the pancreas into the intestine, treating sprue, treating indigestion, providing laxative action, decreasing stomach motility, producing stomach spasmolytic action, increasing intestine motility, treating acute and chronic pancreatitis, degenerated intestine mucous membrane therapy, stimulating gastrointestinal tract exocrinic enzyme secretion, providing antigastrin action, suppressing the formation of and treating ulcers, such as stomach ulcers, enhancing circulation of blood in internal organs, e.g. liver and pancreas, increasing heart force, insufficiency of the heart and circulation system therapy, suppressing and curing liver damage, and treating disturbances in liver function.

Another object is to devise medicament containing at least one such active ingredient. A further object is to provide suitable dosage forms of the medicament. A still further object is to use the medicament in treating conditions which are alleviated or cured by its administration. An additional object is to use relatively non-toxic therapeutically-active and physiologically-acceptable N-acylanilinobutyric acids (or a pharmacologically-acceptable salt thereof) for at least one of the preceding indications. Other objects are apparent from the details which follow.

DETAILS

The medicaments or unit dosage forms contain at least one active ingredient which is an N-acylanilinobutyric acid or a salt thereof and, more particularly, a compound of the formula

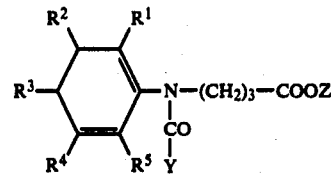

wherein $R^1$ is —H, $C_{1-4}$ alkyl, $C_{1-4}$ alkoxy, $C_{1-4}$ alkylmercapto, halo or trifluoromethyl;

each of $R^2$, $R^4$ and $R^5$, independently, has one of the meanings ascribed to $R^1$;

$R^3$ has one of the meanings ascribed to $R^1$, —OH or benzyloxy;

Y is $C_{1-6}$ alkyl, cycloalkyl having from 3 to 6 ring carbon atoms, unsubstituted or substituted aryl; and Z is —H or an equivalent of a salt-forming cation.

The $C_{1-4}$ alkyl and the alkyl of both the $C_{1-4}$ alkoxy and the $C_{1-4}$ alkylmercapto are branched- or straight-chain alkyl having from 1 to 4 carbon atoms, such as methyl, ethyl, propyl, isopropyl and butyl. Methyl, ethyl, methoxy and ethoxy are preferred substituents selected out of the group consisting of $C_{1-4}$ alkyl, $C_{1-4}$ alkoxy and $C_{1-4}$ alkylmercapto. The $C_{1-6}$ alkyl and the alkyl of the $C_{1-6}$ alkoxy and of the $C_{1-6}$ alkylmercapto comprise $C_{1-4}$ alkyl and alkyls having 5 or 6 carbon atoms.

Halo is chloro, bromo, fluoro or iodo, but preferably chloro or bromo. The cycloalkyl is cyclopropyl, cyclobutyl, cyclopentyl or cyclohexyl.

The only limitations on substituents of the substituted aryl, such as phenyl or naphthyl, are that the respective substituted groups contain a maximum of sixteen carbon atoms and they do not preclude the therapeutic acceptability of the resulting N-acylanilinobutyric acid or its salt. Illustrative substituents include halo, such as chloro and bromo, $C_{1-6}$ alkyl, $C_{1-6}$ alkoxy, $C_{1-6}$ alkylmercapto, carboxyl, sulfonamido, trifluoromethyl and nitro.

Salt-forming cations include such cations as those of alkali metals, e.g. sodium and potassium; those of alkaline earth metals, e.g. calcium and magnesium; that of aluminum; those of pharmacologically acceptable organic bases, e.g. protonated or quaternated organic nitrogenous bases, such as glucosamine; N-methylglucosamine N,N-dimethylglucosamine; ethanolamine; diethanolamine; triethanolamine and ethylenediamine.

The entire disclosure of U.S. Pat. No. 3,780,095 relating to N-acylanilinobutyric acids or effectively non-toxic salts thereof is incorporated herein by reference.

The preferred compounds of formula I are those wherein any substituent on the anilino nucleus is hydrogen, $C_{1-2}$ alkyl, $C_{1-2}$ alkoxy, chloro, bromo or trifluoromethyl; Y is $C_{1-4}$ alkyl or aryl containing a maximum of ten carbon atoms, possibly including such ring substituents as from 1 to 3 chlorine or bromine atoms, alkyl, alkoxy, alkylmercapto, one carboxyl, one sulfonamido, one trifluoromethyl or one nitro; and Z is —H or an equivalent of a cation of sodium, potassium, calcium, magnesium, aluminum, glucosamine, N-methylglucosamine, N,N-dimethylglucosamine, ethanolamine, diethanolamine, triethanolamine or ethylenediamine.

A selected group of preferred active ingredients comprises those wherein the total of all substituents on the anilino nucleus comprises a maximum of ten carbon atoms and preferably at most eight.

Particular significance is attached to the following physiologically-active and pharmacologically-acceptable compounds:

(1) N-(p-chlorobenzoyl)-γ-(m-chloroanilino)butyric acid and its salts
(2) N-benzoyl-γ-(p-anisidino)butyric acid and its salts
(3) N-(p-chlorobenzoyl)-γ-(p-anisidino)butyric acid and its salts
(4) N-(p-chlorobenzoyl)-γ-(p-phenetidino)butyric acid and its salts
(5) N-(p-chlorobenzoyl)-γ-(2,3-dimethylanilino)butyric acid and its salts
(6) N-(p-chlorobenzoyl)-γ-(2,4-dimethoxyanilino)-butyric acid and its salts
(7) N-(p-chlorobenzoyl)-γ-(3,4-dimethoxyanilino)-butyric acid and its salts
(8) N-(o-chlorobenzoyl)-γ-(2,6-dimethylanilino)butyric acid and its salts
(9) N-(p-chlorobenzoyl)-γ-(2,6-dimethylanilino)butyric acid and its salts
(10) N-(p-chlorobenzoyl)-γ-(p-benzyloxyanilino)-butyric acid and its salts
(11) N-(p-chlorobenzoyl)-γ-(p-hydroxyanilino)butyric acid and its salts
(12) N-acetyl-γ-(m-chloroanilino)butyric acid and its salts
(13) N-acetyl-γ-(m-trifluoromethylanilino)butyric acid and its salts of which N-(p-chlorobenzoyl)-γ-(p-anisidino)butyric acid is preferred.

Medicament based on or comprising a pharmacologically-active ingredient of formula I is applied parenterally, preferably as a salt solution, for example subcutaneously, intramuscularly or intraveneously by injection, rectally or preferably orally. Advantageously a pharmaceutical preparation of the active substance is in a unit dose form adapted to suit the desired mode of administration. A uniform dose is, for example, a tablet, a capsule, a suppository or a measured volumetric amount of a powder, a granulate or a solution. The term "unit dose", within the meaning of the present invention, is a physically-determined unit, which comprises an individual quantity of the active component mixed with a pharmaceutical diluent for it or together with a pharmaceutical vehicle. The quantity of active substance is selected so that one or more units are generally needed for individual therapeutic administration.

The unit dose can, however, be capable of being divided up, for example by the use of tablets provided with notches if, for an individual therapeutic administration, only a fraction, e.g. a half or a quarter, of the unit is required.

The pharmaceutical preparations in accordance with the invention comprise, when they are in unit dose form, from 1 to 1,000 mg and, more particularly, advantageously from approximately 5 to 750 mg and, preferably, from approximately 10 to approximately 500 mg of active substance. Therapeutic administration of such pharmaceutical preparations is effected once or several times daily, for example with one dose after each meal and/or in the evening. The administered dose is based on the frequency of administration, the duration of treatment, the nature and severity of the disease and the weight, age and general health of the patient. The daily dose (oral) generally lies between approximately 5 and 50 mg/kg of body weight for mammals.

Pharmaceutical preparations ordinarily consist of effective substance in accordance with the invention and non-toxic pharmaceutically-acceptable medicament vehicles, which are used in solid, semi-solid or liquid form or as encasing materials, for example in form of a capsule, a tablet coating, a sachet or other container, for the therapeutically-active component. A vehicle can be used as a means for promoting the uptake of the medicament by the body, for example as an adjuvant for the formulation, as a sweetening agent, as a flavoring agent, as a dye or as a preserving agent.

Oral dosage forms include tablets, dragees, hard and soft capsules (for example of gelatin), dispersable powders, granulates aqueous and oily suspensions, emulsions, solutions or syrups.

Tablets can incorporate inert diluents, for example calcium carbonate, calcium phosphate, sodium phosphate or lactose; granulation and distributing agents, for example maize starch or alginates; binding agents, for example starch, gelatin or gum acacia; and lubricants, for example aluminum or magnesium stearate, talcum or silicone oil. They can also be additionally provided with a coating, which can be so created to bring about delayed solution and resorption of the medicament in the gastro-intestinal tract and accordingly bring about, for example, improved compatibility or a longer period of action. Gelatin capsules can comprise the medicament mixed with a solid diluent, for example calcium carbonate or kaolin, or an oily one, for example olive oil, ground nut oil or paraffin oil.

Illustrative useful suspending agents include, for example, sodium carboxymethylcellulose, methylcellulose, hydroxypropylcellulose, sodium alginate, polyvinylpyrrolidone, gum tragacanth or gum acacia; useful dispersing and wetting agents include, for example, polyoxyethylene stearate, heptadecaethyleneoxycetanol, polyoxyethylenesorbitol monooleate, polyoxyethylenesorbitane monooleate or lecithin; useful preserving agents include, for example, methyl- or propylhydroxy benzoate; and useful flavoring agents and sweetening agents include, for example, saccharose, lactose, dextrose or invert sugar syrup.

Oily suspensions comprise, e.g., ground nut, olive, sesame, cocoanut or paraffin oil; suitable thickening agents include, e.g., beeswax, paraffin wax or cetyl alcohol. In addition such suspensions optionally contain sweetening agents, flavoring agents and/or antioxidants.

Medicaments mixed with dispersing, wetting and/or suspending agents, such as those previously noted, are optionally incorporated together with sweetening agents, flavoring agents and/or dyes in water-dispersible powders and granulates.

Emulsions comprise, for example, olive, ground nut or paraffin oil (liquid paraffin) in addition to emulsifying agents, such as gum acacia, gum tragacanth, phosphatides, sorbitane monooleate and polyoxyethylenesorbitan monooleate, and sweetening and flavoring agents.

Suppositories, produced with binding agents, e.g. cocoa butter or polyethylene glycols, which fuse at rectal temperature, are useful for rectal administration of the active substances.

For parenteral administration the medicaments can be in the form of sterile isotonic salt solutions or other solutions, inter alia also in 50 g continuous dropping bottles (for continuous intraveneous application).

In addition to the claimed anilinocarboxylic acid compounds the pharmaceutical preparations can comprise one or more other pharmacologically-compatible and therapeutically-active components from other groups of medicaments, for example antacids, tranquilizers, spasmolytics, defoaming agents, laxatives and also ferments, bile acids, antibiotics, vitamins, amino acids and mixtures of fatty acids, etc.

Optionally, the new medicaments can comprise, in addition to the active substances, pharmaceutical vehicle materials for these active substances. The content of active substance of such medicaments comprises from 1 to 95, and preferably from 10 to 85, percent by weight of the finished medicament.

The different dosage forms, otherwise referred to as medicaments, in which the pharmacologically-active N-acylanilinobutyric acid (or salt thereof) is administered are prepared in the same manner that is used for preparing corresponding dosage forms based on other active ingredients. Established procedures and techniques are employed for producing therapeutically-acceptable compositions containing art-recognized essentially pharmaceutically-inert components in standard relevant proportions and combinations.

The term "salts of the acylated anilinocarboxylic acids" is understood herein to mean pharmacologically-compatible salts.

On the basis of the findings indicated, the acylated anilinocarboxylic acid compounds in a dose range of approximately 0.01 to 50, and preferably 0.5 to 20, mg/kg of body weight are suitable for treating a series of illnesses, and more particularly of illnesses of the gastrointestinal tract and of the cardiovascular system.

Pharmacology

1. Pancreas secretion (rat and cat) was examined along the lines of the method described by C. J. Dockray [J. Physiol., 225, 679, (1972)] for the rat and of that described by R. M. Case et al [J. Physiol., 223, 669, (1972)] for the cat.

The pancreas secretion and the bile of narcotized rats (female, 250 to 300 g, stomachs not empty; narcosis: 5 ml/kg of a 25% urethane solution=1.25 g/kg i.m.) and cats (both sexes, stomachs empty, 3 to 4 kg; narcosis: laughing gas and 60 mg/kg i.p. chloralose and 120 mg/kg i.p. urethane; permanent infusion of 0.4 to 2 E/kg/hour secretine=1 to 6 ml/animal/hour, pylorus ligature) were separately transferred to the outside. After an initial period of about 2 hours compounds to be examined were administered intravenously to some and intraduodenally to other animals (volume of injection rat/cat 1 ml/kg). The volume and, respectively, the protein content (amylase, lipase, trypsine) of the fraction for 30 minutes and 15 minutes, respectively, were determined by conventional methods (Boehringer Test Combination 15899).

2. Anti-ulcerogenity was determined according to the method described in German Offenlegungsschrift DT-OS No. 2,118,200. Female Sprague-Dawley rats weighing about 200 g were kept on empty stomach for 24 hours. Then the compounds to be tested were administered orally in the form of their sodium salts in aqueous solution. After 30 minutes 200 mg/kg acetylsalicylic acid (in 10 ml/kg of a 1% tylosc suspension) were administered to cause stomach ulcers. Control groups received the corresponding amount of water instead of the sodium salt solutions. The ulcer rate was determined microscopically 24 hours after the administration of acetylsalicylic acid.

3. The influence of the acylated anilinocarboxylic acids on heart force was determined along the lines of the method of W. Kroneberg et al. [Arzneimittelforschung, 22, 2 (1972)] by determination of the pressure course (isometrically) and pressure increase in the left heart ventricle upon intraveneous administration of the substance to narcotized cats.

4. The blood circulation through the liver was determined by the arterial blood supply (Art. hepatica) along the lines of the method described by Scholtholt (Habilitationsschrift, faculty of medicine, University of Düsseldorf (1969) "Experimental studies with regard to the blood circulation through the liver").

5. The determination of the anti-hepatotoxic and hepatotropic effect, respectively, was carried out by damaging the liver with allyl alcohol or galactosamine.

(a) Damaging due to allyl alcohol was carried out in accordance with the method of Renker et al. [Arzneimittelforschung, 22, 1009 (1972)] and of H. Rauen and Schriewer [Arzneimittelforschung, 21, 1194 (1971)]: female Sprague-Dawley-rats (250 to 300 g) received 3 ml/kg of 1.25% allyl alcohol solution orally 1 hour before the compounds to be tested and the solvent (control) had also been administered orally. 18 hours after the damage due to allyl alcohol a blood sample was taken from the tail (0.5 to 0.7 ml) with slight ether narcosis. The serum enzymes GOT (glutamate oxalacetate transaminase) and GPT (glutamate pyruvate transaminase) were determined with the help of the Boehringer Test Combination (No. 15955/56)—micromethod.

(b) Damaging, due to galactosamine (galactosamine hepatitis) was carried out in accordance with the method described in Arzneimittelforschung 23 Nr. 1a, 159 (1973): Male Sprague-Dawley rats (220 to 300 g) received 200 mg/kg d-galactosamine hydrochloride (Merck, Darmstadt, article no. 4085) intraperitoneally (injection volume 2 ml/kg) 1 hour after oral administration of the compounds to be tested. 24 hours after the damage due to galactosamine a blood sample was taken from the vena orbitalis with slight ether narcosis. The serum enzymes were determined as described under (a).

The pharmacological investigations led to the results collected in Table 1.

Table 1

| Effect/method | (3)* mg/kg | (9)* mg/kg | (4)* mg/kg | (7)* mg/kg | (8)* mg/kg | (12)* mg/kg | (2) mg/kg | (13)* mg/kg | (11)* mg/kg |
|---|---|---|---|---|---|---|---|---|---|
| Increase in pancreas secretion by 50% maximum after i.d. administration (rat) | 1-5 | 0.2-0.5 | 0.1-0.5 | ~1 | ~1 | ~1 | ~0.2 | 0.5-1 | ~0.7 |
| Significantly effective of [ ] mg/kg | [0.05] | [0.01] | [0.05] | [~0.1] | [0.01] | [0.1] | [0.05] | [0.1] | [0.5] |
| Increase in pancreas secretion (cat) by 100% maximum | | | | | | | | | |
| a) pancreas liquid (i.d. administration) | ~10 | | | | | | | | |
| b) protein (enzyme) (i.d. administration) | ~1 | | | | | | | | |
| (i.v. administration) | <10 | | | | | | | | |
| Suppression of the formation of stomach ulcers of rats after oral administration | | | | | | | | | |

Table 1-continued

| Effect/method | (3)* mg/kg | (9)* mg/kg | (4)* mg/kg | (7)* mg/kg | (8)* mg/kg | (12)* mg/kg | (2) mg/kg | (13)* mg/kg | (11)* mg/kg |
|---|---|---|---|---|---|---|---|---|---|
| a) by 100% | ~10 | 1-5 | ~15 | ~5 | ~30 | | 1.5 | | |
| b) by 50% | 1-5 | 0.5-1 | | | | | | | |
| Increase in circulation of blood in internal organs (liver, pancreas) after i.v. administration (cat), effective of | 1-5 | 1 | 1-5 | 1 | 1 | | | | 1-5 |
| Increase in heart force of the heart after i.v. administration (cat) effective of | | 1-5 | 1 | 1-5 | 1 | 2.5 | | | ~1 |
| Anti-hepatotoxic action (oral administration of substance; inhibition of serum enzyme increase (after allyl alcohol) by 25% (GOT/GPT) | | | | | | | | | |
| a) damage due to allyl alcohol | 5-10 | ~10 | ~10 | 50 | | | 5-10 | | ~10 |
| b) damage due to galactosamine | ~20 | 10-20 | ~10 | ~20 | ~20 | | ~50 | | |

*Substances (see list on page 6 of the text) are administered as sodium salts.

From the preceding description one skilled in the art can use the present invention troughout its scope. The following exemplary compositions are merely illustrative of embodiments employed for selected modes of administration. They neither limit the nature or types of compositions that are practical for administering the subject pharmacologically-active ingredients nor restrict the modes of administration available for compositions based on such pharmacologically-active ingredients.

EXAMPLE 1

Ampoules with 600 mg N-(p-chlorobenzoyl)-γ-(p-anisidino) butyric acid [clanobutine] [3] batch of 250 kg:
[3]: 15.000 kg
Aqueous solution of sodium hydroxide (10% by weight NaOH): 17.251 kg
1,2-Propyleneglycol: 25.000 kg
Sodium disulfite: 0.0625 kg
Aqua bidestillata: 250.000 kg 25.0 kg of 1,2-propyleneglycol and 150.0 kg of water are mixed, 150.0 kg of [3] are added and the sodium hydroxide solution is slowly poured into the mixture with stirring. After complete dissolution the pH-value is brought up to 7.5-8.0. The sodium disulfite is added, the mixture is stirred until complete dissolution and then filled up with the residual water. The solution is filled in 10 ml-ampoules which are sterilized at 120° C. for 30 minutes in an autoclave.

EXAMPLE 2

Ampoules with 600 mg N-(p-chlorobenzoyl)-γ-(2,6-dimethylanilino)butyric acid [9], batch of 250 kg:
[9]: 15.000 kg
Aqueous solution sodium hydroxide (10% by weight NaOH): 16.440 kg
1,2-Propyleneglycol: 50.000 kg
Aqua bidestillata: ad 250.000 kg 50.0 kg of 1,2-propylenglycol and 150.0 kg of water are mixed, 15.0 kg of [9] are added with stirring and the sodium hydroxide solution is slowly poured into the mixture. After complete dissolution the pH-value is brought up to 8.0. The mixture is stirred until complete dissolution and then filled up with the residual water. The solution is filled in 10 ml-ampoules which are sterilized at 120° C. for 30 minutes in an autoclave.

EXAMPLE 3

Tablets with 50 mg of N-(p-chlorobenzoyl)-γ-(2,6-dimethylanilino)butyric acid [9]:

| | |
|---|---|
| [9] | 25,000 kg |
| Lactose | 35,000 kg |
| Cornstarch | 26,000 kg |
| Polyvinylpyrrolidone (molecular weight ~25,000) | 2,500 kg |
| Carboxymethylcellulose | 8,000 kg |
| Talc | 2,500 kg |
| Magnesium stearate | 1,000 kg |
| | 100,000 kg |

[9], lactose and cornstarch are granulated with polyvinylpyrrolidone in about 6 liters of water. The granulate is screened through a screen with 1.25 mm width of mesh. After drying carboxymethylcellulose, talc and magnesium stearate are added. The dry granulate is pressed into tablets with a diameter of 8 mm, a weight of 200 mg and a hardness of 5 to 6 kg.

Tablets containing N-(p-chlorobenzoyl)-γ-(p-phenetidino) butyric acid and N-benzoyl-γ-(p-anisidino) butyric acid, respectively, are prepared accordingly.

EXAMPLE 4

Tablets with 100 mg of N-(p-chlorobenzoyl)-γ-(p-anisidino) butyric acid [3]:

| | |
|---|---|
| [3] | 40,000 kg |
| Lactose | 24,000 kg |
| Cornstarch | 16,000 kg |
| Polyvinylpyrrolidone (molecular weight ~25,000) | 4,000 kg |
| Carboxymethylcellulose | 10,000 kg |
| Talc | 4,000 kg |
| Magnesium stearate | 2,000 kg |
| | 100,000 kg |

[3], lactose and cornstarch are granulated with polyvinylpyrrolidone in about 5.5 liters of water. The granulate is screened through a screen with 1.25 mm width of mesh. After drying carboxymethylcellulose, talc and magnesium stearate are added. The dry granulate is pressed into tablets with a diameter of 9 mm, a weight of 250 mg and a hardness of 4 to 5 kg.

N-(p-chlorobenzoyl)-γ-(2,6-dimethylanilino)butyric acid and N-(p-chlorobenzoyl)-γ-(p-phenetidino)butyric acid and N-benzoyl-γ-(p-anisidino)butyric acid, respectively, and pressed into tablets containing 100 mg of active compound.

EXAMPLE 5

Tablets with 300 mg of N-(p-chlorobenzoyl)-γ-(p-anisidino)butyric acid [3]:

| | |
|---|---|
| [3] | 60,000 kg |
| Lactose | 12,000 kg |
| Cornstarch | 8,000 kg |
| Polyvinylpyrrolidone (molecular weight ~25,000) | 4,000 kg |
| Carboxymethylcellulose | 10,000 kg |
| Talc | 4,000 kg |
| Magnesium stearate | 2,000 kg |
| | 100,000 kg |

[3], lactose and cornstarch are granulated with polyvinylpyrrolidone in about 6 liters of water. The granulate is screened through a screen with 1.25 mm width of mesh. After drying carboxymethylcellulose, talc and magnesium stearate are added. The dry granulate is pressed into tablets with a diameter of 11 mm, a weight of 500 mg and a hardness of 6 to 7 kg.

EXAMPLE 6

Prepare 100 cc. of an elixir, containing 16.2 mg of the sodium salt of N-(p-chlorobenzoyl)-γ-(p-anisidino)butyric acid [3] in each 5 cc., from the following ingredients:

[3]: 3.24 grams
Citric acid: 0.1 gram
F.D.C. Red No. 1: 0.04 gram
Saccharin: 0.1 gram
Sucrose: 200 grams
Oil of spearmint: 0.1 gram
Oil of wintergreen: 0.1 gram
Polysorbate 80, U.S.P.: 1.0 gram
Glycerin: 150 cc.
Ethanol, 95%: 200 cc.
Water, q.s.: 1000 cc.

Dissolve the sugar in 450 cc. of water and add the citric acid, color and [3] thereto. Add the saccharin to the mixture of alcohol and glycerin and stir until dissolved. Mix the flavors with the polysorbate 80; incorporate the resulting mixture into the saccharin solution, and admix the product with the aqueous sugar solution of [3], adding sufficient water to make up 1000 cc. Replacing [3] by the same amount of the sodium salt of N-(p-chlorobenzoyl)-γ-(2,4-dimethoxyanilino)butyric acid results in the preparation of the corresponding similar-useful elixir.

EXAMPLE 7

Prepare 1000 capsules for oral administration, each containing 100 mg of N-(p-chlorobenzoyl)-γ-(2,6-dimethylanilino)butyric acid [9], from the following ingredients:

[9]: 100 grams
Citric acid: 1 gram
Pluronic, F-68: 40 grams
Sodium lauryl sulfate: 20 grams
Lactose: 238 grams
Magnesium stearate: 1 gram Mix together the [9], citric acid, Pluronic, sodium lauryl sulfate and lactose. Pass the resulting mixture through a No. 80 screen. Add magnesium stearate, mix and encapsulate into the proper size 2-piece gelatin capsule.

Replacing [9] by the same amount of N-(o-chlorobenzoyl)-γ-(2,6-dimethylanilino)butyric acid results in the preparation of corresponding similarly-useful capsules.

EXAMPLE 8

Prepare 1000 suppositories, each containing 100 mg of N-benzoyl-γ-(p-anisidino)butyric acid [2], from the following ingredients:

[2], micronized: 100 grams
Polyethylene glycol 1000: 1500 grams
Polyethylene glycol 4000, USP, q.s.: 2000 grams Prepare a slurry of the [2] with a portion of the melted polyethylene glycol mixture. Pass the slurry through a suitable colloid mill until it is free of grittiness. Add sufficient melted polyethylene glycol mixture to bring the batch to final weight. Pour the melted mix, maintaining uniformity, into appropriately prepared molds and allow to cool.

Replacing [2] by the same amount of N-(p-chlorobenzoyl)-γ-(p-benzyloxyanilino)butyric acid results in the preparation of corresponding similarly-useful suppositories.

EXAMPLE 9

Tablets with 50 mg of N-(p-chlorobenzoyl)-γ-(2,6-dimethylanilino)butyric acid [9] and 10 mg diethylaminocarbethoxybicyclohexyl hydrochloride [14]:

| | |
|---|---|
| [9] | 25,000 kg |
| [14] | 5,000 kg |
| Lactose | 32,000 kg |
| Cornstarch | 24,000 kg |
| Polyvinylpyrrolidone (molecular weight ~25,000) | 2,500 kg |
| Carboxymethylcellulose | 8,000 kg |
| Talc | 2,500 kg |
| Magnesium stearate | 1,000 kg |
| | 100,000 kg |

[9], [14], lactose and cornstarch are granulated with polyvinylpyrrolidone in about 6 liters of water. The granulate is screened through a screen with 1.25 mm width of mesh. After drying carboxymethylcellulose, talc and magnesium stearate are added. The dry granulate is pressed into tablets with a diameter of 8 mm, a weight of 200 mg and a hardness of 5 to 6 kg.

Tablets containing N-(p-chlorobenzoyl)-γ-(p-phentidino)butyric acid and N-benzoyl-γ-(p-anisidino)butyric acid, respectively, are prepared accordingly.

EXAMPLE 10

Tablets with 100 mg of N-(p-chlorobenzoyl)-γ-(p-anisidino)butyric acid [3] and 100 mg of tetracycline hydrochloride [15]:

| | |
|---|---|
| [9] | 10,000 kg |
| [16] | 1,400 kg |
| [17] | 1,500 kg |
| [18] | 5,000 kg |
| Citric acid | 0,100 kg |
| Pluronic, F-68 | 4,000 kg |
| Sodium lauryl sulfate | 2,000 kg |
| Lactose | 25,800 kg |
| Magnesium stearate | 0,200 kg |
| | 50,000 kg |

Mix together the [9], [16], [17], [18], citric acid, Pluronic, sodium lauryl sulfate and lactose. Pass the resulting mixture through a No. 80 screen. Add magnesium stearate, mix and encapsulate into the proper Size 00-piece gelatin capsule.

Replacing [9] by the same amount of N-(o-chlorobenzoyl)-γ-(2,6-dimethylanilino)butyric acid [8] results in the preparation of corresponding similarly-useful capsules.

The invention and its advantages are readily understood from the preceding description. It is apparent that various changes may be made in the formulations, unit doses and regimen of administration without departing from the spirit and scope of the invention or sacrificing its material advantages. The hereinbefore-described medicaments (formulations for administration) are merely illustrative embodiments of the invention, which is primarily directed to new uses of the indicated active ingredients.

What is claimed is:

1. A process which comprises administering to a warm-blooded animal having a pancreas insufficiency an amount of medicament composition sufficient to alleviate such insufficiency, the medicament composition having a plurality of ingredients and comprising from one to 95 percent by weight of at least one physiologically-active and pharmacologically-acceptable N-acylanilinobutyric acid or a substantially non-toxic salt thereof.

2. A process according to claim 1 wherein the medicament composition comprises, as at least one active ingredient, a compound of the formula

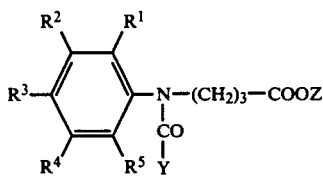

wherein
$R^1$ is a member selected from the group consisting of —H, alkyl having from 1 to 4 carbon atoms, alkoxy having from 1 to 4 carbon atoms, alkylmercapto having from 1 to 4 carbon atoms, halo and trifluoromethyl;
each of
$R^2$, $R^4$ and $R^5$ is, independently, one of the meanings of $R^1$;
$R^3$ is, independently, one of the meanings of $R^1$, —OH or benzyloxy;
Y is $C_{1-6}$ alkyl, cycloalkyl having from 3 to 6 carbon atoms, unsubstituted or substituted aryl and
Z is —H or an equivalent of a salt-forming cation;
the total number of carbon atoms in all substituents of substituted aryl being at most sixteen.

3. A process according to claim 1 wherein the warm-blooded animal is a mammal.

4. A process according to claim 2 wherein the active ingredient is N-(p-chlorobenzoyl)-γ-(p-anisidino)-butyric acid or a physiologically-acceptable salt thereof.

5. A process according to claim 1 which comprises administering to a warm-blooded animal deficient in exocrinic pancreas enzyme secretion into the intestine an amount of the medicament composition which is sufficient to stimulate such secretion.

6. A process according to claim 1 which comprises administering to a warm-blooded animal afflicted with acute or chronic pancreatitis an amount of the medicament composition which is sufficient to counteract such affliction.

7. A process according to claim 2 wherein the active ingredient is N-(p-chlorobenzoyl)-γ-(m-chloroanilino)-butyric acid or a physiologically-acceptable salt thereof.

8. A process according to claim 2 wherein the active ingredient is N-benzoyl-γ-(p-anisidino)butyric acid or a physiologically-acceptable salt thereof.

9. A process according to claim 2 wherein the active ingredient is N-(p-chlorobenzoyl)-γ-(p-phenetidino)-butyric acid or a physiologically-acceptable salt thereof.

10. A process according to claim 2 wherein the active ingredient is N-(p-chlorobenzoyl)-γ-(2,3-dimethylanilino)butyric acid or a physiologically-acceptable salt thereof.

11. A process according to claim 2 wherein the active ingredient is N-(p-chlorobenzoyl)-γ-(2,4-dimethoxyanilino)butyric acid or a physiologically-acceptable salt thereof.

12. A process according to claim 2 wherein the active ingredient is N-(p-chlorobenzoyl)-γ-(3,4-dimethoxyanilino)butyric acid or a physiologically-acceptable salt thereof.

13. A process according to claim 2 wherein the active ingredient is N-(o-chlorobenzoyl)-γ-(2,6-dimethylanilino)butyric acid or a physiologically-acceptable salt thereof.

14. A process according to claim 2 wherein the active ingredient is N-(p-chlorobenzoyl)-γ-(2,6-dimethylanilino)butyric acid or a physiologically-acceptable salt thereof.

15. A process according to claim 2 wherein the active ingredient is N-(p-chlorobenzoyl)-γ-(p-benzyloxyanilino)butyric acid or a physiologically-acceptable salt thereof.

16. A process according to claim 2 wherein the active ingredient is N-(p-chlorobenzoyl)-γ-(p-hydroxyanilino)butyric acid or a physiologically-acceptable salt thereof.

17. A process according to claim 2 wherein the active ingredient is N-acetyl-γ-(m-chloroanilino)butyric acid or a physiologically-acceptable salt thereof.

18. A process according to claim 2 wherein the active ingredient is N-acetyl-γ-(m-trifluoromethylanilino)-butyric acid or a physiologically-acceptable salt thereof.

19. A process according to claim 1 wherein the N-acylanilinobutyric acid is a member selected from the group consisting of:
N-(p-chlorobenzoyl)-γ-(m-chloroanilino)butyric acid,
N-benzoyl-γ-(p-anisidino)butyric acid,
N-(p-chlorobenzoyl)-γ-(p-anisidino)butyric acid,
N-(p-chlorobenzoyl)-γ-(p-phenetidino)butyric acid,
N-(p-chlorobenzoyl)-γ-(2,3-dimethylanilino)butyric aicd,
N-(p-chlorobenzoyl)-γ-(2,4-dimethoxyanilino)butyric acid,
N-(p-chlorobenzoyl)-γ-(3,4-dimethoxyanilino)butyric acid,
N-(o-chlorobenzoyl)-γ-(2,6-dimethylanilino)butyric acid,
N-(p-chlorobenzoyl)-γ-(2,6-dimethylanilino)butyric acid,
N-(p-chlorobenzoyl)-γ-(p-benzyloxyanilino)butyric acid,
N-(p-chlorobenzoyl)-γ-(p-hydroxyanilino)butyric acid,
N-acetyl-γ-(m-chloroanilinobutyric acid and
N-acetyl-γ-(m-trifluoromethylanilino)butyric acid.

* * * * *